US010342422B2

(12) United States Patent
Hathaway et al.

(10) Patent No.: US 10,342,422 B2
(45) Date of Patent: Jul. 9, 2019

(54) RETINAL THICKNESS

(71) Applicant: Cellview Imaging Inc., Toronto OT (CA)

(72) Inventors: Mark Hathaway, Toronto (CA); Rishard Weitz, Toronto (CA)

(73) Assignee: Cellview Imaging Inc. (CA)

( * ) Notice: Subject to any disclaimer, the term of this patent is extended or adjusted under 35 U.S.C. 154(b) by 2 days.

(21) Appl. No.: 15/431,150

(22) Filed: Feb. 13, 2017

(65) Prior Publication Data

US 2018/0228367 A1   Aug. 16, 2018

(51) Int. Cl.
A61B 3/10 (2006.01)
A61B 3/00 (2006.01)
A61B 3/12 (2006.01)

(52) U.S. Cl.
CPC .......... *A61B 3/1005* (2013.01); *A61B 3/0025* (2013.01); *A61B 3/102* (2013.01); *A61B 3/1025* (2013.01); *A61B 3/1225* (2013.01)

(58) Field of Classification Search
CPC ..... A61B 3/1005; A61B 3/102; A61B 3/1025; A61B 3/1225; A61B 3/0025
USPC ........................................................ 351/206
See application file for complete search history.

(56) References Cited

U.S. PATENT DOCUMENTS

2014/2187848    8/2014  Wax

FOREIGN PATENT DOCUMENTS

CA    2595324 A1    7/2006
WO    2016004508 A1    1/2016

OTHER PUBLICATIONS

Drexler, Wolfgang, et al, "Ultrahigh-resolution ophthalmic optical coherenece tomography," Nat. Med. Apr. 2001; 7(4); 502-507, Web Oct. 18, 2017 <https://www.ncib.nlm.nih.gov/pmc/articles/PMC1950821/>.
Wojtkowski, Maciej, et al, "In vivo human retinal imaging by Fourier Domain optical coherence tomography," J. Biomedical Optics Jul. 2002; 7(3), 457-463.
Mujat, Mircea, et al, "Retinal Nerve Fiber Layer Thickness Map Determined from Optical Coherence Tomography Images," Optics Express, Nov. 14, 2005, pp. 9480-9491, vol. 13 No. 23, Optical Society of America.

*Primary Examiner* — Jack Dinh
(74) *Attorney, Agent, or Firm* — Laubscher & Laubscher, P.C.

(57) ABSTRACT

A method is provided for determining the thickness of a retina. A single beam is used to illuminate the retina of a patient. Interference between reflections off different layers within the retina cause autocorrelation in the returned signal. A spectrometer produces a frequency spectrum of the beam reflected by the retina, and an FFT applied to the frequency spectrum produces a spatial domain signal (SDS). Autocorrelation within the reflected beam results in edges within the spatial domain signal, and the spatial coordinate of the SDS at which the power of the SDS drops precipitously indicates the distance between the nerve fiber layer (NFL) and the layers between the inner segment/outer segment (IS/OS) and the retinal pigment epithelium (RPE), the dominant scatterers. By analyzing autocorrelation, a single beam can be used. This avoids the problem of movement of the patient, arising in the use of a standard OCT interferometer, resulting in a simpler and less expensive technique of measuring retinal thickness.

20 Claims, 4 Drawing Sheets

RETINAL THICKNESS

FIELD OF INVENTION

This invention relates to measurement of the thickness of a retina.

BACKGROUND

Retinal thickness in the central retina is frequently used to detect diseases in their early stages, and to monitor the effectiveness of treatment. Generally, images and data obtained with optical coherence tomography (OCT) systems are used. A standard spectral OCT system typically splits light from a single source into two parts, each of which traverses a different path in an interferometer. One path, called the reference path, simply introduces a variable delay into the beam travelling the reference path. The other path, called the object path, travels to and scatters back from a patient's eye. The light scattered back from the patient's eye is mixed with light from the reference path to produce an interference signal. The interference signal is analyzed with a spectrometer. For a usable OCT signal to be produced the two paths must be matched in length. However, this means that patient movement tends to be an issue. Complicated image processing must be performed in order to compensate for patient movement when determining the retinal thickness when using a standard OCT system.

There is a need to provide a method of measuring retinal thickness using a simpler procedure, and which preferably does not depend on lack of movement by the patient.

SUMMARY

According to one embodiment of the invention, a method is provided for determining the thickness of a retina. The retina is illuminated with a beam of light. A beam reflected by the retina is received, and a frequency spectrum signal is produced using the reflected beam. A Fast Fourier Transform (FFT) is applied to the frequency spectrum signal to produce a spatial domain signal. The thickness of the retina is determined from a spatial measurement of the spatial domain signal at which the power of the spatial domain signal drops to a floor power.

According to another embodiment of the invention, a method of diagnosing retinal and/or ocular diseases in a patient is provided. A retina of the patient is illuminated with a beam of light. A beam reflected by the retina is received, and a frequency spectrum signal is produced using the reflected beam. A Fast Fourier Transform (FFT) is applied to the frequency spectrum signal to produce a spatial domain signal. The thickness of the retina is determined from a spatial measurement of the spatial domain signal at which the power of the spatial domain signal drops to a floor. If the determined thickness of the retina is larger than a threshold, then it is concluded that retinal and/or ocular disease is present.

By using the autocorrelation signal within a reflected beam to determine the thickness of a patient's retina, movement by the patient need not be compensated for. Diagnosis of various retinal diseases is thereby simpler and more effective.

BRIEF DESCRIPTION OF THE DRAWINGS

The features and advantages of embodiments of the invention will become more apparent from the following detailed description of the preferred embodiment(s) with reference to the attached figures, wherein.

It is noted that in the attached figures, like features bear similar labels.

DETAILED DESCRIPTION OF THE PREFERRED EMBODIMENTS

The autocorrelation signal within a beam of light reflected by a patient's retina is produced by different reflections of a transmitted beam, the transmitted beam reflecting off different layers of the retina and interfering with each other. The dominant scatterers in the retina are the nerve fiber layer (NFL) and the layers between the inner segment/outer segment (IS/OS) and the retinal pigment epithelium (RPE). Although mixing occurs between all layers, the dominant signal is produced by interference between light reflected off these two regions. Since reflections from each component are encoded in the same beam at the same time because of autocorrelation, movement by the patient is not an issue. This simplifies image processing.

Figure 1:
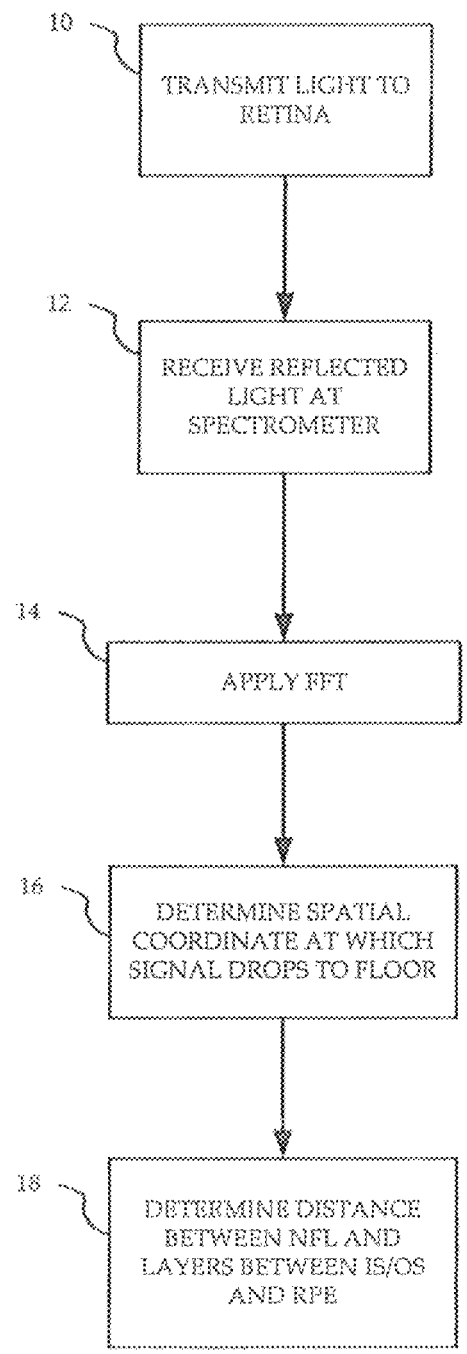
FIG. 1 shows a flowchart of a method by which the thickness of a retina is determined according to one embodiment of the invention.

Referring to FIG. 1, a flowchart of a method of determining the thickness of a retina according to one embodiment of the invention is shown. At step 10 a beam of light is transmitted towards a patient's retina. At step 12 a reflected beam from the patient's retina is received at a spectrometer. The step 12 of receiving a reflected beam from the patient's retina is carried out over an integration time.

The spectrometer generates a frequency spectrum signal from the beam received at step 12. The frequency spectrum generated by the spectrometer contains multiple frequencies due to the distributed signals in the received beam, which in turn are due to distributed scattering by features throughout the depth of the retina. At step 14 a processor applies a Fast Fourier Transform (FFT) to the frequency spectrum signal and generates a spatial domain signal.

Figure 2A:
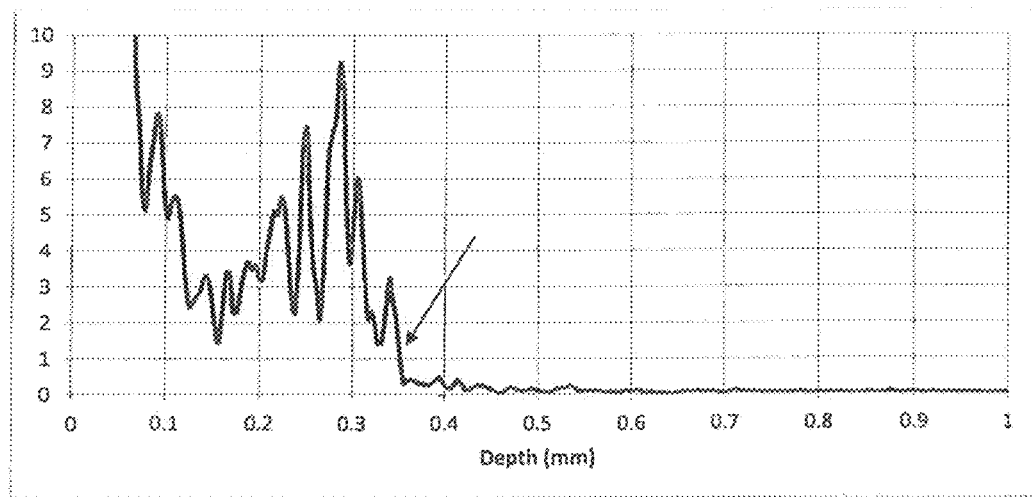
FIG. 2a shows an example plot of the power of an autocorrelation signal versus spatial dimension for a sample reflected signal is shown according to one embodiment of the invention.
Figure 2B:
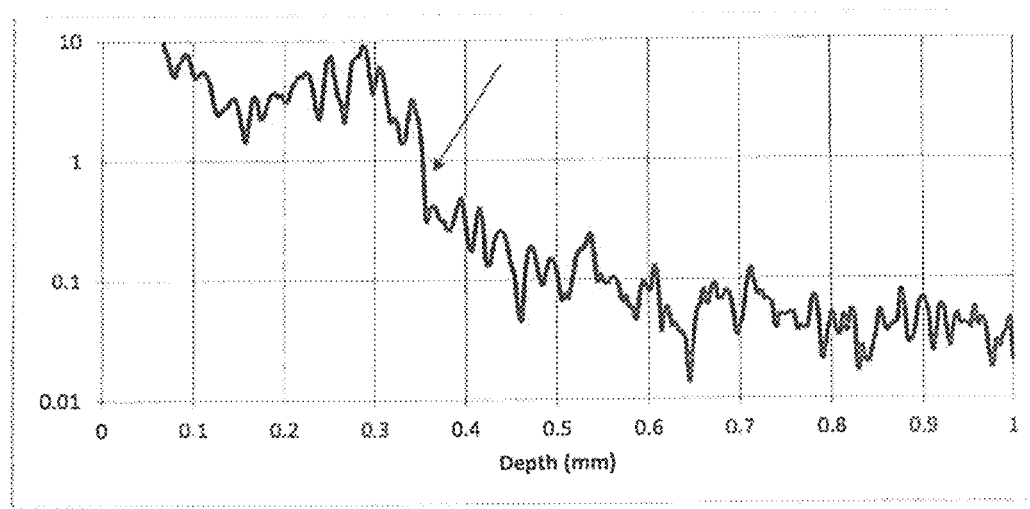
FIG. 2b shows the plot of FIG. 2a in which the power of the autocorrelation signal is represented logarithmically.

At step 16 the processor determines the spatial coordinate at which the power of the spatial domain signal drops to a floor of the power of the signal. A sample plot is shown in FIGS. 2a and 2b to better illustrate this. In each figure, the spatial coordinate of the spatial domain signal (the horizontal axis of the plot) produced at step 14 has been converted into units representing the distance relative to the retina. The vertical axis indicates the power of the spatial domain signal. As can be seen, between 0.00 mm and about 0.35 mm the spatial domain signal has significant power, due to autocorrelation of the signal reflected by the retina. At distances greater than about 0.35 mm there is very little power within the spatial domain signal. The low power beyond about 0.35 mm can viewed as the floor of the power of the signal. In FIG. 2a the vertical axis of the plot shows the power of the spatial domain signal. FIG. 2b illustrates the same plot where the vertical axis represents the logarithm of the power of the spatial domain signal. In this representation of the power of the signal, the drop to the floor can be more clearly seen as occurring at the distance at which there is the sharpest drop in the logarithm of the power.

The spatial coordinate at which the power of the spatial domain signal drops to the floor of the signal can be determined using edge detection techniques, or other signal processing techniques such as, but not limited to, threshold detection.

The sharp drop in power occurs for a depth at which there stops being significant autocorrelation within the signal reflected from the retina. As explained above, this occurs when there is no interference between the signal reflected from the NFL and the signal reflected from the layers between the IS/OS and the RPE. Once the processor determines the spatial coordinate at which this sharp drop occurs, then at step 18 the distance between the NFL and the layers between the IS/OS and the RPE can be determined, and the thickness of the retina deduced.

Any of a number of different systems can be used to carry out the method described above with reference to FIG. 1. Because the interference is between different reflections within the same beam, an interference pattern does not require interference with a separate beam. In one embodiment, an optical coherence tomography (OCT) system is used to measure the thickness of a retina. In an OCT system, an OCT signal is produced by interference between a reference beam and a reflected beam, the reflected beam being the reflection of an object beam off a patient's retina. The autocorrelation signal is present in the reflected beam reaching the interferometer. The autocorrelation signal is usually considered noise, and OCT systems are normally designed to suppress the autocorrelation signal relative to the OCT signal by suitable choice of reference beam power. This is possible because the OCT signal is a function of the reference beam power and the object beam power, whereas the autocorrelation signal is a function only of the object beam power. However according to this embodiment of the invention, measurement of the autocorrelation signal in the object beam is desired, and there is no need, or even desire, to suppress the autocorrelation signal.

Figure 3:
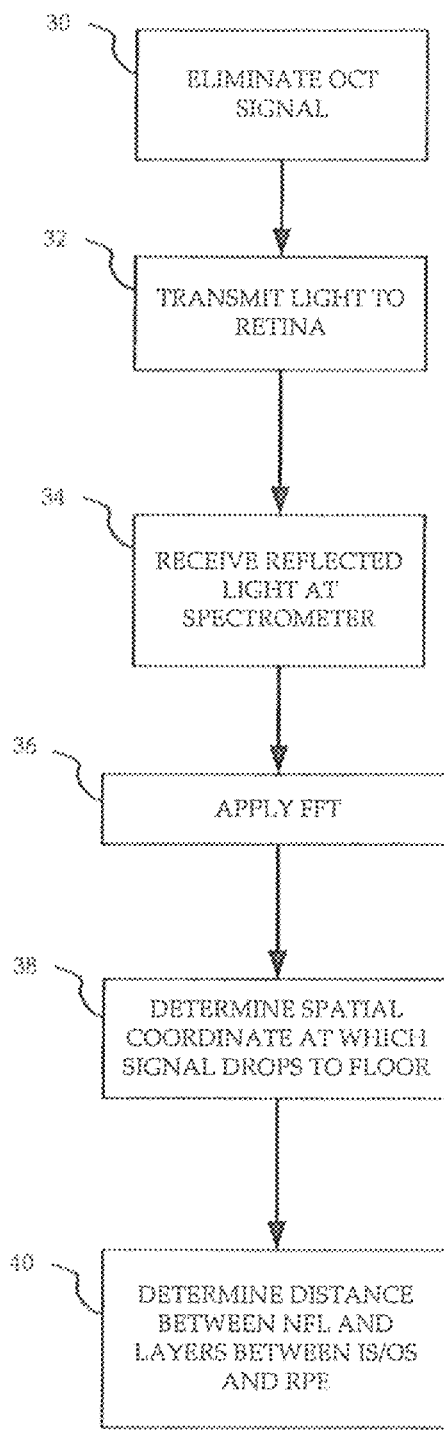
FIG. 3 shows a flowchart of a method by which the thickness of a retina is determined using an OCT system according to one embodiment of the invention.

Referring to FIG. 3, a flowchart of a method of determining the thickness of a retina using an OCT system according to one embodiment of the invention is shown. At step 30 the possibility of an OCT signal is eliminated, so that the only signal reaching the spectrometer of the OCT system will be the reflected object arm beam. The OCT signal is most easily eliminated by setting the reference path to an extreme position, such as at a maximum or a minimum length, resulting in no interference between the reference beam and the reflected beam within the object path. However other means of eliminating an OCT signal may be used, such as by attenuating the reference arm power.

At step 32 a beam of light is transmitted towards a patient's retina along the object arm of the OCT system. At step 34 a reflected beam from the patient's retina is received at a spectrometer. Normally this beam would result from interference between a signal in the reference arm and a signal in the object arm, the latter being reflected from the patient's retina. However, since the OCT signal has been eliminated at step 32, such as by extending the reference path to an extreme position, the only beam received by the spectrometer is the reflected beam within the object arm, and the autocorrelation signal is visible as more than just noise.

The spectrometer generates a frequency spectrum signal from the beam received at step 34. The frequency spectrum generated by the spectrometer contains multiple frequencies due to the distributed signals in the received beam, which in turn is due to distributed scattering by features throughout the depth of the retina. At step 36 a processor applies a Fast Fourier Transform (FFT) to the frequency spectrum signal and generates a spatial domain signal. At step 38 the processor locates the spatial coordinate of the spatial domain signal at which the power of the spatial domain signal drops to a floor of the power of the signal. As explained above, a sharp edge arises because of interferometry between the signal reflected from the NFL and the signal reflected from the layers between the IS/OS and the RPE. Once this spatial coordinate is located, then at step 40 the distance between the NFL and the layers between the IS/OS and the RPE can be determined, and the thickness of the retina deduced.

In another embodiment, a scanning laser ophthalmoscopy (SLO) system is used to measure the thickness of a retina. The avalanche photodiode (APD) or photomultiplier tube (PMT) normally found in an SLO system is replaced with a spectrometer in order to produce a frequency spectrum of the beam reflected from a patient's retina. Alternatively, the APD or PMT can be kept in place in order that the SLO functions can still be used, but part of the returned beam is split and sent to a spectrometer in order to produce a frequency spectrum of the reflected beam. Unlike an OCT system, there is no reference beam contributing to the beam received by the spectrometer and the spectrometer used in such an embodiment needs to be more sensitive than that used in an OCT system. However, this greater sensitivity can be achieved with longer integration times and much less expensive charge-coupled devices (CCDs) or complementary metal-oxide-semiconductor (CMOS) arrays than are used in OCT systems. The step of receiving a reflected beam from the patient's retina is carried out over this longer integration time. A processor then determines the thickness of the retina from the reflected beam as described above.

In yet another embodiment, a fixed point measurement system is used to measure the thickness of a retina. The high sensitivity requirement of the spectrometer required for clear detection of the autocorrelation signal can be achieved with use of a 2D camera in the spectrometer, such as a low cost video CCD, in order to analyze light returned from the fixed point.

In yet another embodiment, the retinal thickness is determined using a line scan system. A 2D-camera is employed in the spectrometer. A beam is transmitted towards an eye, and then optical components smear out the transmitted beam so that it hits the retina along a line across the retina. The signal is reflected from multiple fixed points on the retina at the same time. A plurality of frequency spectra is produced, each frequency spectra corresponding to one point from the line across the retina. An FFT is applied to each frequency spectra, thereby producing a plurality of spatial domain signals (SDSs). A plurality of spatial measurements is determined, each spatial measurement being that at which the power of a corresponding one of the SDSs falls to a floor power of the SDS. Such spatial measurements can be determined using edge detection techniques, or other signal processing techniques such as, but not limited to, threshold detection. In short, the method described above with reference to FIG. 1 is carried out in parallel by the processor, once for each point imaged by the line scan system.

Figure 4:
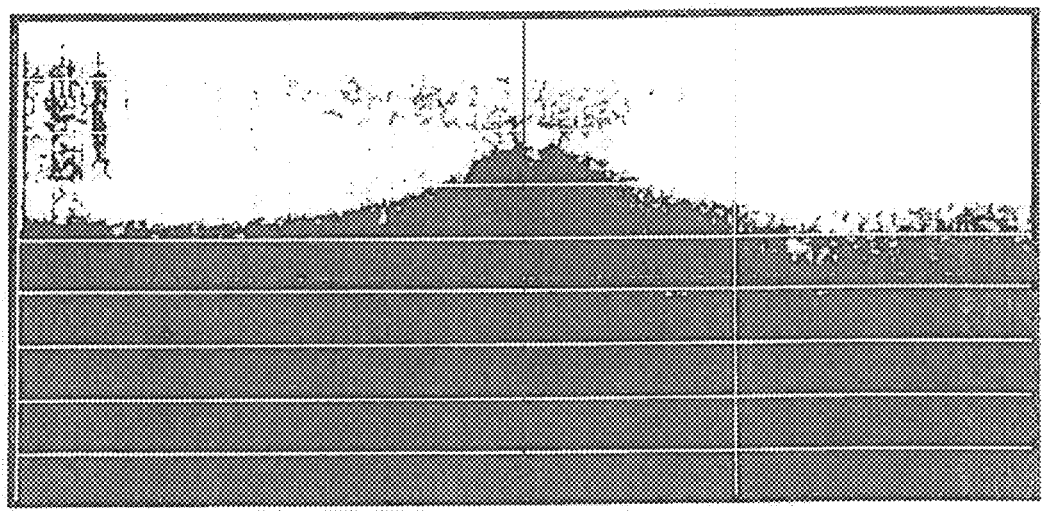
FIG. 4 shows an example photograph of the intensity of the autocorrelation signal as a function of position across the retina and depth within the eye.

Alternatively, the plurality of spatial domain signals can be used to generate a two-dimensional image, an example of which is shown in FIG. 4.

In FIG. 4, the power of the spatial domain signal for a given position across the retina is indicated by the intensity of the plot, the brightness of the diagram indicating the intensity. The horizontal axis indicates the position along a line of the retina. The vertical axis indicates the depth within the retina, and corresponds generally with the horizontal axis shown in FIG. 2a and FIG. 2b. Edge detection techniques, or other signal processing techniques such as, but not limited to, threshold detection, can be used to locate the distance at which the signal drops sharply, as in the signal dimension signal shown in FIG. 2a and FIG. 2b, but the edge is even more apparent in the two-dimensional image shown in FIG. 4 as the edge between the light and dark regions. A thickness measure can then be determined for each of a plurality of points in the image as the distance between the located edge and a fixed edge for the point at which there is significant power in the SDS, e.g. the top edge of the data set shown in FIG. 4.

In either case, the "thickness of the retina" can comprise a plurality of thickness measures, one for each point along across the retina, a plurality of thickness measures determined only for a subset of these points, thickness measure for only one of these points, or a collective measure based on the statistics of these measures (e.g. their average).

A thickness map can also be generated by determining thicknesses of the retina across multiple lines across the retina.

In the embodiments described above, the thickness of the retina is derived from an autocorrelation signal using a spectrometer. Alternatively, regular interferometry and variable path imbalance can be used to measure the thickness of the retina directly. As yet another alternative, a tunable laser and the Fourier domain can be used.

The methods described above for determining the thickness of a retina can be used in methods for screening and diagnosing of various retina and ocular diseases. Such diseases include diabetic retinopathy, diabetic macular edema, age-related macular degeneration (AMD), cystoid macular edema, central serous retinopathy, central retinal vein occlusion, central retinal artery occlusion, and glaucoma. Retinal thickness increases dramatically in such diseases due to death of cells of specific inner or outer layers of the retina due to the above diseases at more progressive stages. Accordingly, in one embodiment of the invention the methods described above for determining the thickness of a retina are preliminary steps in a method for screening and/or diagnosing such diseases.

The logic of the methods described above may be stored as instructions stored on a non-transitory computer-readable storage medium in a form executable by a computer processor, although in the embodiment in which an OCT system is used to carry out the method the elimination the OCT signal may be carried out manually instead. The logic of the methods described above may also be stored as instructions within a memory accessible by a processor, such that when read and executed by the processor they cause the processor to carry out the methods. The processor may be implemented by a general purpose processor, a network processor, a digital signal processor, an ASIC, or multiple such devices.

The embodiments presented are exemplary only and persons skilled in the art would appreciate that variations to the embodiments described above may be made without departing from the spirit of the invention. The scope of the invention is solely defined by the appended claims.

We claim:

1. A method of determining the thickness of a retina, comprising:
   illuminating the retina with a beam of light;
   receiving a reflected beam of light from the retina;
   producing a frequency spectrum signal from the reflected beam;
   applying a Fast Fourier Transform (FFT) to the frequency spectrum signal to produce a spatial domain signal (SDS); and
   determining the thickness of the retina from a spatial coordinate of the SDS at which the power of the SDS drops to a floor power.

2. The method of claim 1 wherein determining the thickness of the retina comprises:
   determining the distance between the nerve fiber layer (NFL) and the layers between the inner segment/outer segment (IS/OS) and the retinal pigment epithelium (RPE) from the spatial coordinate of the SDS at which the power of the SDS drops to the floor power; and
   deducing the thickness of the retina from the determined distance between the NFL and the layers between the IS/OS and the RPE.

3. The method of claim 1 further comprising eliminating the possibility of interference between a signal in the reference arm of an optical coherence tomography (OCT) system and a signal in the object arm of the OCT system, and wherein the beam of light used to illuminate the retina is the signal in the object arm of the OCT system.

4. The method of claim 2 further comprising eliminating the possibility of interference between a signal in the reference arm of an optical coherence tomography (OCT) system and a signal in the object arm of the OCT system, and wherein the beam of light used to illuminate the retina is the signal in the reference arm of the OCT system.

5. The method of claim 1 wherein the spatial coordinate at which the power of the SDS drops to a floor power is determined using edge detection on the SDS.

6. The method of claim 1 wherein the beam of light used to illuminate the retina is the transmitted beam in a scanning laser ophthalmoscopy (SLO) system.

7. The method of claim 1 wherein the beam of light used to illuminate the retina is the transmitted beam in a fixed point measurement system.

8. The method of claim 1 wherein receiving a reflected beam of light comprises receiving a line of reflected light, the line of reflected light having been reflected from a line across the retina;
   wherein producing a frequency spectrum comprises producing a plurality of frequency spectra, one frequency spectrum for each of a plurality of points within the line of reflected light, each of the plurality of points within the line of reflected light corresponding to one of a plurality of points in the retina;
   wherein applying a FFT comprises applying a FFT separately to each of the plurality of frequency spectra so as to produce a plurality of SDSs, each SDS corresponding to one of the plurality of frequency spectra;
   and wherein determining the thickness of the retina comprises determining the thickness of the retina at each of the plurality of points across the retina, the thickness of the retina at each of the plurality of points being determined from the spatial coordinate at which the power of the SDS corresponding to the point in the retina drops to a floor power of the SDS.

9. The method of claim 1 wherein receiving a reflected beam of light comprises receiving a line of reflected light, the line of reflected light having been reflected from a line across the retina;
   wherein producing a frequency spectrum comprises producing a plurality of frequency spectra, one frequency spectrum for each of a plurality of points within the line of reflected light, each of the plurality of points within the line of reflected light corresponding to one of a plurality of points in the retina;

wherein applying a FFT comprises applying a FFT separately to each of the plurality of frequency spectra so as to produce a plurality of SDSs, each SDS corresponding to one of the plurality of frequency spectra; and wherein determining the thickness of the retina comprises:

locating an edge within an image formed of the plurality of the SDSs using signal processing; and determining the thickness of the retina based on the distance between the located edge and a fixed edge of the image.

10. The method of claim 9 wherein locating the edge within the image comprises using edge detection on the image.

11. The method of claim 9 wherein locating the edge within the image comprises using threshold detection of the image.

12. A method of diagnosing retinal and/or ocular diseases in a patient, comprising:

illuminating a retina of the patient with a beam of light;
receiving a reflected beam of light from the retina;
producing a frequency spectrum signal from the reflected beam of light;
applying a Fast Fourier Transform (FFT) to the frequency spectrum signal to produce a spatial domain signal (SDS);
determining the thickness of the retina from a spatial coordinate of the SDS at which the power of the SDS drops to a floor power; and
concluding that retinal and/or ocular disease is present if the determined thickness of the retina is larger than a threshold.

13. The method of claim 12 wherein determining the thickness of the retina comprises:

determining the distance between the nerve fiber layer (NFL) and the layers between the inner segment/outer segment (IS/OS) and the retinal pigment epithelium (RPE) from the spatial coordinate of the SDS at which the power of the SDS drops to a floor power; and deducing the thickness of the retina from the determined distance between the NFL and the layers between the IS/OS and the RPE.

14. The method of claim 12 further comprising eliminating the possibility of interference between a signal in the reference arm of an optical coherence tomography (OCT) system and a signal in the object arm of the OCT system, and wherein the beam of light used to illuminate the retina is the signal in the object arm of the OCT system.

15. The method of claim 12 wherein the spatial coordinate at which the power of the SDS drops to a floor power is determined as the spatial coordinate at which there is the sharpest drop in the logarithm of the power of the SDS.

16. The method of claim 12 wherein the beam of light used to illuminate the retina is the transmitted beam in a scanning laser ophthalmoscopy (SLO) system.

17. The method of claim 12 wherein the beam of light used to illuminate the retina is the transmitted beam in a fixed point measurement system.

18. The method of claim 12 wherein receiving a reflected beam of light comprises receiving a line of reflected light, the line of reflected light having been reflected from a line across the retina;

wherein producing a frequency spectrum comprises producing a plurality of frequency spectra, one frequency spectrum for each of a plurality of points within the line of reflected light, each of the plurality of points within the line of reflected light corresponding to one of a plurality of points in the retina;

wherein applying a FFT comprises applying a FFT separately to each of the plurality of frequency spectra so as to produce a plurality of SDSs, each SDS corresponding to one of the plurality of frequency spectra;

and wherein determining the thickness of the retina comprises determining the thickness of the retina at each of the plurality of points across the retina, the thickness of the retina at each of the plurality of points being determined from the spatial coordinate at which the power of the SDS corresponding to the point in the retina drops to a floor power of the SDS.

19. The method of claim 12 wherein receiving a reflected beam of light comprises receiving a line of reflected light, the line of reflected light having been reflected from a line across the retina;

wherein producing a frequency spectrum comprises producing a plurality of frequency spectra, one frequency spectrum for each of a plurality of points within the line of reflected light, each of the plurality of points within the line of reflected light corresponding to one of a plurality of points in the retina;

wherein applying a FFT comprises applying a FFT separately to each of the plurality of frequency spectra so as to produce a plurality of SDSs, each SDS corresponding to one of the plurality of frequency spectra; and wherein determining the thickness of the retina comprises:

locating an edge within an image formed of the plurality of the SDSs; and determining the thickness of the retina based on the distance between the located edge and a fixed edge of the image.

20. The method of claim 19 wherein locating the edge within the image comprises using edge detection on the image.

* * * * *